United States Patent [19]

Dutton et al.

[11] Patent Number: 4,592,871

[45] Date of Patent: Jun. 3, 1986

[54] N-IMIDOYLTHIO(METHYL)CARBAMATES

[75] Inventors: Fred E. Dutton; Stephen J. Nelson, both of Kalamazoo, Mich.

[73] Assignee: The Upjohn Company, Kalamazoo, Mich.

[21] Appl. No.: 616,504

[22] Filed: May 31, 1984

Related U.S. Application Data

[62] Division of Ser. No. 436,245, Oct. 25, 1982, Pat. No. 4,473,580.

[51] Int. Cl.$^4$ .................. C07C 149/14; C07C 119/16
[52] U.S. Cl. ........................................... 558/2; 558/1; 558/6
[58] Field of Search .......................... 260/453.1, 453.7

[56] References Cited

U.S. PATENT DOCUMENTS

| 3,679,733 | 11/1970 | Brown | 260/479 |
|---|---|---|---|
| 3,843,689 | 5/1972 | Brown | 260/346.2 |
| 4,004,031 | 7/1975 | Drabek | 424/327 |
| 4,081,536 | 2/1977 | Nelson | 424/211 |
| 4,148,910 | 12/1976 | Hartmann et al. | 424/285 |
| 4,333,883 | 7/1981 | Nelson | 260/544 |

OTHER PUBLICATIONS

U.S. application Ser. No. 436,245.
R. Roger and D. Neilson, Chem. Rev. 61, p. 179 (1961).
G. Olah, Synthesis 1973 (11), p. 661.

*Primary Examiner*—Henry R. Jiles
*Assistant Examiner*—Robert C. Whittenbaugh
*Attorney, Agent, or Firm*—Kenneth A. Weber

[57] ABSTRACT

This invention pertains to some new organic compounds, to a process for preparing them, and to formulations of them suitable for pesticidal use. The invention is more particularly directed to imidic acid derivatives of N-thio(methyl)carbamates.

11 Claims, No Drawings

N-IMIDOYLTHIO(METHYL)CARBAMATES

This application is a divisional of U.S. application Ser. No. 436,245, filed Oct. 25, 1982, now U.S. Pat. No. 4,473,580, issued Sept. 25, 1984.

SUMMARY OF THE INVENTION

This invention pertains to some new organic compounds, to a process for preparing them, and to formulations of them suitable for pesticidal use. The invention is more particularly directed to imidic acid derivatives of N-thio(methyl)carbamates.

Substituted-thio derivatives of methylcarbamate pesticides are known, and U.S. Pat. Nos. 4,081,536, 4,148,910, 4,004,031 and 3,679,733 can be referred to for relevant status of the art. Insofar as is presently known, no one has prepared imidic acid derivatives of N-thio(methyl)carbamates.

Some of the objectives of this invention include the obtainment of methylcarbamate pesticides having an effectiveness equal to or greater than that of the parent compounds against pests, such methylcarbamate pesticides having reduced mammalian toxicity, reduced phytotoxicity, and longer residual action. Other worthwhile objectives will be recognized by those skilled in the art.

DETAILED DESCRIPTION OF THE INVENTION

The indicated N-imidoylthio(methyl)carbamate pesticides of this invention are represented by the schematic formula I wherein R is selected from the group consisting of the moiety having the formula Ia wherein $R_3$, $R_4$ and $R_5$ are the same or different and are selected from the group consisting of hydrogen, lower-alkyl of one to five carbon atoms, inclusive, halogen, lower-alkoxy of one to five carbon atoms, inclusive, lower-alkylthio of one to five carbon atoms, inclusive, dialkylamino with each alkyl the same or different and having one to three carbon atoms, inclusive, and $-N=CHN(CH_3)_2$;

the moiety having formula Ib wherein A and B are the same or different and are selected from the group consisting of lower-alkyl of one to five carbon atoms, inclusive, lower-alkylthio of one to five carbon atoms, inclusive, monocyano substituted lower-alkylthio of one to five carbon atoms, inclusive, phenylthio wherein phenyl is unsubstituted or substituted with one to three substituents, same or different, selected from the group consisting of halogen and lower-alkyl of one to five carbon atoms, inclusive, cyano, alkoxy having one to five carbon atoms, inclusive, phenyl and hydrogen, with the proviso that when B is hydrogen, A is of the formula Ic wherein $R_6$ is selected from the group consisting of alkyl of one to three carbon atoms, inclusive, and phenyl; $R_7$ is alkyl of one to three carbon atoms, inclusive; $R_8$ is selected from the group consisting of alkyl of one to three carbon atoms, inclusive, and $SR_9$, wherein $R_9$ is alkyl and is the same alkyl group as $R_6$, and taking $R_6$ and $R_9$ together with the atoms of Ic to which they are attached form a dithio heterocyclic of the formula Id wherein n is 2 or 3 and the alkylene portion of the ring is unsubstituted or substituted with one or two methyl groups; A and B taken together with the carbon atoms to which they are attached form a dithio heterocyclic of the formula Ie wherein m is 2 or 3 and the alkylene portion of the ring is unsubstituted or substituted with one or two methyl groups; and the moiety If;

$R_1$ and $R_2$ are the same or different and are selected from the group consisting of one to ten carbon atoms, inclusive, alkyl phenyl, substituted phenyl, phenyl substituted lower-alkyl, and cycloalkyl;

X is oxygen or sulfur.

In the foregoing designation of variables, "lower-alkoxy" means methoxy, ethoxy, propoxy, isopropoxy, butoxy, pentoxy, and the further isomeric forms thereof. Likewise, "lower-alkylthio" means in addition to lower-alkyl, hexyl, heptyl, octyl, nonyl, decyl and the isomeric forms thereof.

Lower-alkyl" means methyl, ethyl, propyl, butyl, pentyl, and the isomeric forms thereof; while "cycloalkyl" means cyclopropyl, cyclobutyl, cyclopentyl, and cyclohexyl optionally substituted with methyl, ethyl, and propyl to a total of nine carbon atoms; "alkyl" means in addition to lower-alkyl, hexyl, heptyl, octyl, nonyl, decyl and the isomeric forms thereof.

"Phenyl substituted lower-alkyl" means benzyl, phenethyl, phenpropyl, phenbutyl, phenpentyl, and isomeric forms thereof.

"Substituted-phenyl" means lower-alkyl-, lower alkoxy-, halogen-, nitro-, and cyano-substituted phenyl. There can be combinations of substituents such as 4-propyl-2-methyl, 2-chloro-4-methyl, 3,4-diethoxy, 3-cyano-4-ethoxy, and the like. Practically speaking, the substituted-phenyl group is limited to a total of ten carbon atoms, e.g., 4-isobutylphenyl.

"Substituted phenoxy" means lower-alkyl, lower-alkoxy, halogen, nitro, and cyano substituted phenoxy. There can be combinations of substituents such as 4-propyl-2-methyl, 2-chloro-4-methyl, 3,4-diethoxy, 3-cyano-4-ethoxy, phenoxy and the like. The substituted phenoxy is limited to a total of ten carbon atoms, e.g., 4-isobutylphenoxy.

"Substituted thiophenoxy" means lower-alkyl, lower-alkoxy, halogen, nitro, and cyano substituted thiophenoxy. There can be combinations of substituents such as 4-propyl-2-methyl-, 2-chloro-4-methyl, 3,4-diethoxy, and the like. The substituted thiophenoxy is limited to a total of ten carbon atoms, e.g., 4-isobutylthiophenoxy and the like.

The new N-imidoylthio(methyl)carbamate pesticidal compounds of this invention having formula I can be prepared in accordance with the process of the invention by reacting a selected oximino or phenolic precursor of formula III with an N-imidoylthio(methyl)carbamoyl fluoride of formula II. A schematic representation of the reaction, preparing compounds of formula I as an example, is as follows:

wherein R, $R_1$, $R_2$ and X are the same as above.

The compound having the formula III is known or readily prepared by methods known or obvious to one of skill in the art.

The reaction is effected from $-20°$ C. to $100°$ C., preferably $0°$ C. to $35°$ C. in a two phase reaction medium consisting of a suitable inert organic solvent and an aqueous solution of an alkali metal hydroxide of from 0.01N to 6N, preferably 0.1N to 2N concentration.

The reaction is facilitated by the presence of a phase transfer catalyst. Illustrative of suitable organic solvents are methylene chloride, ether and toluene. Illustrative of suitable alkali metal hydroxides are sodium hydroxide and potassium hydroxide. Illustrative of suitable phase transfer catalysts are cetylbenzyldimethylammonium chloride, tetrabutylammonium chloride and benzyltrimethylammonium chloride. Methylene chloride is a particularly effective solvent.

Alternatively, this reaction can be performed in a single phase reaction medium consisting of a suitable inert organic solvent and a suitable acid acceptor from −20° C. to 100° C., preferably 0° C. to 35° C. Illustrative of inert organic solvents are methylene chloride, tetrahydrofuran, ethyl acetate, toluene and acetonitrile. Illustrative of suitable acid acceptors are trialkylamines (e.g., triethylamine), pyridine and lutidine.

The desired compounds of formula I are recovered and purified according to conventional methods. Filtration, solvent evaporation, chromatography, crystallization and combinations thereof are employed. Some of the compounds are obtained as crystals while others are purified as oils.

The N-imidoylthio(methyl)carbamoyl fluorides of formula II are prepared by reacting the corresponding imidic acid esters of formula IV wherein $R_1$ and $R_2$ are as defined above with N-chlorothio(methyl)carbamoyl fluoride. This is shown schematically as follows:

IV+ClS-N(CH$_3$)C(O)F→II wherein $R_1$, $R_2$ and X are the same as above.

The reaction is effected from −50° C. to 50° C., preferably −20° C. to 25° C. in the presence of a suitable acid acceptor and an inert organic solvent. Illustrative of suitable acid acceptors are trialkylamines (e.g., triethylamine), pyridine and lutidine. Illustrative of inert organic solvents are methylene chloride, chloroform, toluene, diethylether, tetrahydrofuran and hexane. Conventional methods are used in the isolation of the product II. Methylene chloride is a particularly effective solvent.

The imidic acid esters IV can be readily prepared by the methods described in the prior art; for example, see R. Roger and D. Neilson, Chem. Rev. 61, p. 179 (1961) and G. Olah, Synthesis 1973 (11), p. 661.

N-chlorothio(methyl)carbamoyl fluoride is prepared according to the procedure given in U.S. Pat. No. 4,333,883 and modifications thereof.

An alternate synthesis can be performed which also gives products of formula I shown previously. In this synthesis the imidic acid ester of formula IV is caused to react with an N-chlorothio(methyl)carbamate of formula V. The alternate synthesis may be shown schematically as follows:

IV+V→I wherein R, $R_1$, $R_2$ and X are the same as above.

The reaction is effected in an inert organic medium from −50° C. to 50° C., preferably −20° C. to 20° C. in the presence of a suitable acid acceptor. Illustrative of inert organic solvents are methylene chloride, chloroform, tetrahydrofuran, and toluene. Illustrative of suitable acid acceptors are trialkylamine (e.g., triethylamine), pyridine and lutidine. Conventional methods are used in the isolation and purification of the product. The N-chlorothio(methyl)carbamates of formula V can be readily prepared by methods described in the prior art; for example, U.S. Pat. No. 3,843,689.

The preferred compounds of this invention are those having the formula I wherein R is Ib, wherein A and B are the same or different and are selected from the group consisting of lower-alkyl of one to five carbon atoms, inclusive, lower-alkylthio of one to five carbon atoms, inclusive, monocyano substituted alkylthio of one to five carbon atoms, inclusive, phenylthio wherein phenyl is unsubstituted or substituted with one to three substituents, same or different, selected from the group consisting of halogen and lower-alkyl of one to four carbon atoms, inclusive, cyano, alkoxy having one to five carbon atoms, inclusive, phenyl, inclusive, or wherein R is If; and $R_1$, X and $R_2$ are defined above.

The following described preparations of new compounds according to formula I are indicative of the scope of this invention and are not to be construed as limitative. Those skilled in the art will promptly recognize appropriate variations from the procedure both as to oximino and phenolic precursors as well as reaction conditions and techniques. These examples indicate the best modes presently known to the inventor.

PREPARATION 1

Phenyl N-[[methyl[fluorocarbonyl]amino]-thio]-2-methylpropiothioimidate

The hydrochloride salt of compound IV (wherein $R_1$ is isopropyl, X is sulfur, and $R_2$ is phenyl)+ClS-N(CH$_3$)C(O)F→II (having corresponding substituents $R_1$, X, and $R_2$).

Phenyl 2-methylpropiothioimidate hydrochloride (11.7 g., 54.4 mmoles) and N-chlorothio(methyl)carbamoyl fluoride (7.8 g., 54.4 mmoles) are added in turn to methylene chloride (100 ml). To this mixture under an atmosphere of dry nitrogen at −10° is added a solution of triethylamine (17 ml, 120 mmoles) in methylene chloride (30 ml) over a period of 4 minutes with rapid stirring. The reaction mixture is stirred for 90 minutes at −10° and then poured into ice-cold water (100 ml). The mixture is shaken briefly and the layers separated. The organic phase is washed in turn with 2N HCl (100 ml) and saturated NaHCO$_3$ (100 ml) then dried over anhydrous MgSO$_4$. The solvent is removed under reduced pressure. There is thus obtained the desired reactant as a clear, light yellow oil. The nmr spectrum is consistent with the desired structure.

EXAMPLE 1

Phenyl N-[[methyl[[[2,3-dihydro-2,2-dimethyl-7-benzofuranyl]oxy]carbonyl]amino]thio]-2-methylpropiothioimidate II (wherein $R_1$ is isopropyl, X is S, and $R_2$ is phenyl)-+ROH (wherein R is If)→I (having corresponding substituents for $R_1$, X, $R_2$ and R).

To a solution of phenyl N-[[methyl[fluorocarbonyl]amino]thio]-2-methylpropiothioimidate (7.8 g, 27 mmoles) as prepared in Preparation 1 and cetylbenzyldimethylammonium chloride (0.9 g) in methylene chloride (150 ml) is added a solution of 2,3-dihydro-2,2-dimethyl-7-benzofuranol (4.5 g, 27 mmoles) in 0.18N sodium hydroxide (150 ml). The two-phase reaction mixture is stirred vigorously at ambient temperature for 90 minutes. The layers are separated and the organic phase dried over anhydrous sodium sulfate. Removal of the solvent gives a clear brown oil. This material is transferred to a column of silica gel and the chromatogram developed with a solvent mixture consisting of 8% ethylacetate in Skellysolve B. From the appropriate fraction there is obtained a white solid which is recrystallized from hexane to give the product phenyl N-[[methyl[[[2,3-dihydro-2,2-dimethyl-7- benzofuranyl]oxy]carbonyl]amino]thio]-2-methyl-propiothioimidate as a white crystalline solid, mp 104°–106°.

Analysis: Calculated for $C_{22}H_{26}N_2O_3S_2$: C, 61.37; H, 6.09; N, 6.51. Found: C, 61.54; H, 6.12; N, 6.45.

The nmr and ir spectra are consistent with the expected structure.

EXAMPLE 2

Isopropyl N-[[methyl[[[2,3-dihydro-2,2-dimethyl-7-benzofuranyl]oxy]carbonyl]amino]thio]benzimidate The hydrochloride salt of the compound IV (wherein $R_1$ is phenyl, X is O, and $R_2$ isopropyl)+V (wherein R is If)→I (having corresponding substituents, $R_1$, X, $R_2$ and R).

To a solution of isopropyl benzimidate hydrochloride (18.0 g, 90 mmoles) in methylene chloride (100 ml) at 0° under an atmosphere of dry nitrogen is added a solution of triethylamine (28 ml, 200 mmoles) in a small stream with stirring. To this mixture is added a solution of 2,3-dihydro-2,2-dimethyl-7-benzofuranyl N-chlorothio(methyl)carbamate (26 g, 90 mmoles) in methylene chloride (80 ml) in a dropwise fashion. The reaction mixture is stirred for two hours at 0° and then washed in turn with water, 2N hydrochloric acid and saturated sodium bicarbonate. The organic phase is dried over anhydrous magnesium sulfate and the solvent is removed under reduced pressure. The residue is poured onto a column of silica gel. Elution of the column with a solvent consisting of 15 parts ether and 85 parts Skellysolve B gives from the appropriate fraction isopropyl N-[[methyl[[[2,3-dihydro-2,2-dimethyl-7-benzofuranyl]oxy]carbonyl]amino]thio]benzimidate as a yellow oil.

Analysis: Calculated for $C_{22}H_{26}N_2O_4S$: C, 63.75; H, 6.32; N, 6.76. Found: C, 62.16; H, 6.26; N, 6.41.

The nmr and ir spectra are consistent with the desired structure.

PREPARATIONS 2–7

Starting with the known compound N-chlorothio(methyl)carbamoyl fluoride and the appropriate imidic acid ester or thioimidic acid ester (either of which may be in the form of its hydrochloric acid salt), the following new N-imidoylthio(methyl)carbamoyl fluorides II are prepared by procedures similar to Preparation 1:

ethyl N-[[methyl[fluorocarbonyl]amino]thio]-2,6-dichlorobenzimidate, whose nmr spectrum is consistent with the structure assigned, ethyl N-[[methyl[fluorocarbonyl]amino]thio]-benzimidate, whose nmr spectrum is consistent with the structure assigned, methyl N-[[methyl[fluorocarbonyl]amino]thio]-benzimidate, whose nmr spectrum is consistent with the structure assigned, n-butyl N-[[methyl[fluorocarbonyl]amino]thio]-benzimidate, whose nmr spectrum is consistent with the structure assigned, n-butyl N-[[methyl[fluorocarbonyl]amino]thio]-2-methylpropionimidate, whose nmr spectrum is consistent with the structure assigned, phenyl N-[[methyl[fluorocarbonyl]amino]thio]-benzothioimidate, whose nmr spectrum is consistent with the structure assigned.

EXAMPLES 3–6

Starting with the known compound 2,3-dihydro-2,2-dimethyl-7-benzofuranol and the appropriate N-imidoylthio(methyl)carbamoyl fluoride II, the new N-imidoylthio(methyl)carbamates I are prepared by procedures similar to Example 1. In addition to the elemental analyses given, nmr and ir spectra were consistent with the expected structures. The new N-imidoylthio(methyl)carbamates I are as follows:

methyl N-[[methyl[[[2,3-dihydro-2,2-dimethyl-7-benzofuranyl]oxy]carbonyl]amino]thio]benzimidate as a yellow oil Analysis: Calculated for $C_{20}H_{22}N_2O_4S$: C, 62.16; H, 5.74; N, 7.25. Found: C, 62.21; H, 5.87; N, 7.17.

n-butyl N-[[methyl[[[2,3-dihydro-2,2-dimethyl-7-benzofuranyl]oxy]carbonyl]amino]thio]benzimidate as a yellow oil Analysis: Calculated for $C_{23}H_{28}N_4O$: C, 64.46; H, 6.59; N, 6.54. Found: C, 63.98; H, 6.57; N, 6.22.

n-butyl N-[[methyl[[[2,3-dihydro-2,2-dimethyl-7-benzofuranyl]oxy]carbonyl]amino]thio]-2-methylpropionimidate as a yellow oil Analysis: Calculated for $C_{20}H_{30}N_2O_4S$: C, 60.89; H, 7.66; N, 7.10. Found: C, 60.33; H, 7.67; N, 6.90.

phenyl N-[[methyl[[[2,3-dihydro-2,2-dimethyl-7-benzofuranyl]oxy]carbonyl]amino]thio]benzothioimidate as a yellow oil Analysis: Calculated for $C_{25}H_{24}N_2O_3S_2$: C, 64.63; H, 5.21; N, 6.03. Found: C, 64.22; H, 5.31; N, 5.98.

EXAMPLES 7–10

Starting with the known compound methyl N-hydroxyethanimidothioate and the appropriate N-imidoylthio(methyl)carbamoyl fluoride II, the new N-imidoylthio(methyl)carbamates I are prepared by procedures similar to Example 1. In addition to the elemental analyses given, spectral data were consistent with the expected structures. The new N-imidoylthio(methyl)carbamates I are as follows:

ethyl N-[[methyl[[[[1-(methylthio)ethylidene]amino]oxy]carbonyl]amino]thio]-2,6-dichlorobenzimidate as a yellow oil Analysis: Calculated for $C_{14}H_{17}Cl_2N_3O_3S_2$: C, 40.98; H, 4.18; N, 10.24; Cl, 17.28. Found: C, 40.94; H, 4.33; N, 9.85; Cl, 17.43.

ethyl N-[[methyl[[[[1-(methylthio)ethylidene]amino]oxy]carbonyl]amino]thio]benzimidate as a yellow oil.

Analysis: Calculated for $C_{14}H_{19}N_3O_3S_2$: C, 49.25; H, 5.61; N, 12.31. Found: C, 48.46; H, 6.00; N, 12.12.

phenyl N-[[methyl[[[[1-(methylthio)ethylidene]amino]oxy]carbonyl]amino]thio]benzothioimidate as a white crystalline solid, mp 139–141

Analysis: Calculated for $C_{18}H_{19}N_3O_2S_3$: C, 53.31; H, 4.72; N 10.36. Found: C, 53.29; H, 4.72; N, 10.42.

phenyl N-[[methyl[[[[1-(methylthio)ethylidene]amino]oxy]carbonyl]amino]thio]-2-methylpropiothioimidate as a white crystalline solid, mp 90°–92°

Analysis: Calculated for $C_{15}H_{21}N_3O_2S_3$: C, 48.49; H, 5.70; N, 11.31. Found: C, 48.48; H, 5.65; N, 11.28.

Utilizing a procedure similar to Preparation 1 but further substituting the appropriate imidic acid ester or thioimidic acid ester (either of which may be in the form of its hydrochloric acid salt), the additional following new N-imidoylthio(methyl)carbamoyl fluorides having formula II are prepared:

n-decyl N-[[methyl[fluorocarbonyl]amino]-thio]-2-phenylethanthioimidate,
phenbutyl N-[[methyl[fluorocarbonyl]amino]-thio]-2-ethylhexanimidate,
3,5-dimethylphenyl N-[[methyl[fluorocarbonyl]amino]-thio]ethanimidate,
2-fluorophenyl N-[[methyl[fluorocarbonyl]-amino]thio]benzimidate,
3-cyano-4-ethoxyphenyl N-[[methyl[fluorocarbonyl]amino]thio]-2-methylpropiothioimidate,
methyl N-[[methyl[fluorocarbonyl]amino]thio]-2-phenylpropionimidate,
2-chloro-4-nitrophenyl N-[[methyl[fluorocarbonyl]amino]thio]-2-methylpropiothioimidate,
2-propyl N-[[methyl[fluorocarbonyl]amino]-thio]-2,4-dinitrobenzimidate,
2-fluoro-4-isobutylphenyl N-[[methyl[fluorocarbonyl]amino]thio]ethanimidate.

Starting with the known compounds of formula III described above and appropriate compounds of formula II, the following corresponding new N-imidoylthio(methyl)carbamates having formula I are prepared by procedures similar to Example 1:

phenyl N-[[methyl[[[4-(dimethylamino)-3,5-xylyl]oxy]carbonyl]amino]thio]-2-methylpropiothioimidate,
isopropyl N-[[methyl[[[2-isopropoxyphenyl]-oxy]carbonyl]amino]thio]benzimidate,
methyl N-[[methyl[[[2-isopropoxyphenyl]oxy]-carbonyl]amino]thio]benzimidate,
n-butyl N-[[methyl[[[3-isopropylphenyl]oxy]-carbonyl]amino]thio]benzimidate,
n-butyl N-[[methyl[[[[1-(methylthio)ethylidene]amino]oxy]carbonyl]amino]thio]-2-methylpropiothioimidate,
phenyl N-[[methyl[[[[1-(methylthio)ethylidene]amino]oxy]carbonyl]amino]thio]benzothioimidate,
n-butyl N-[[methyl[[[[1-(methylthio)ethylidene]amino]oxy]carbonyl]amino]thio]-2-methylpropionimidate,
decyl N-[[methyl[[[2,3-dihydro-2,2-dimethyl-7-benzofuranyl]oxy]carbonyl]amino]thio]-2-phenylethanthioimidate,
phenbutyl N-[[methyl[[[2,3-dihydro-2,2-dimethyl-7-benzofuranyl]oxy]carbonyl]amino]thio]-2-ethylhexanimidate,
3,5-dimethylphenyl N-[[methyl[[[2,3-dihydro-2,2-dimethyl-7-benzofuranyl]oxy]carbonyl]amino]-thio]ethanimidate,
2-fluorophenyl N-[[methyl[[[2,3-dihydro-2,2-dimethyl-7-benzofuranyl]oxy]carbonyl]amino]thio]-benzimidate,
3-cyano-4-ethoxyphenyl N-[[methyl[[[2,3-dihydro-2,2-dimethyl-7-benzofuranyl]oxy]carbonyl]-amino]thio]-2-methylpropiothioimidate,
methyl N-[[methyl[[[2,3-dihydro-2,2-dimethyl-7-benzofuranyl]oxy]carbonyl]amino]thio]-2-phenylpropionimidate,
2-chloro-4-nitrophenyl N-[[methyl[[[2,3-dihydro-2,2-dimethyl-7-benzofuranyl]oxy]carbonyl]-amino]thio]-2-methylpropiothioimidate,
2-propyl N-[[methyl[[[2,3-dihydro-2,2-dimethyl-7-benzofuranyl]oxy]carbonyl]amino]thio]-2,4-dinitrobenzimidate,
3-fluoro-4-isobutylphenyl N-[[methyl[[[2,3-dihydro-2,2-dimethyl-7-benzofuranyl]oxy]carbonyl]-amino]thio]ethanimidate.

Compounds of formula I such as each named above are alternatively prepared by procedures similar to Example 2 and discussed and schematically shown above as IV+V→I. In this synthesis an appropriate imidic acid ester or thioimidic acid ester both of formula IV is caused to react with a correspondingly appropriate N-chlorothio(methyl)carbamate of formula V.

The compounds of formula I are effective pesticides that can be used to control invertebrate pests in agriculture, industry, and around the home as shown by tests against insect pests.

Representative pest species have been used in the tests illustratively, order Lepidoptera, more specifically, the southern armyworm (SAW), (*Prodenia eridania*, Cramer), the tobacco budworm (TBW), (*Heliothis virescens*), and the cabbage looper ova (CLO), (*Trichoplusia ni*); order Diptera, more specifically, the housefly (HF), (*Musca domestica*, Linnaeus) or the yellow-fever mosquito (YFM), (*Aedes aegypti*); order Coleoptera, more specifically, the mexican bean beetle (MBB), (*Epilachna varivestis*, Mulsant); order Acarina, more specifically, the two-spotted spider mite (TSSM), (*Tetranychus urticae*, Koch).

Efficacy against invertebrate pests has been demonstrated at low concentrations, as low as 0.015 parts per million (ppm) depending upon the specific pest used. Some invertebrate animal pests will be more sensitive to the compounds than others, and others might be quite resistant. In general, the compounds of formula I are used at concentrations ranging from about 30 to about 6000 ppm. The following test results show efficacy for representative compounds of the invention.

Phenyl N-[[methyl[[[2,3-dihydro-2,2-dimethyl-7-benzofuranyl]oxy]carbonyl]amino]thio]-2-methylpropiothioimidate

| Insect | Rate | % Mortality |
| --- | --- | --- |
| SAW | 15.6 ppm | 100 |
| CLO | 15.6 ppm | 100 |
| HF | 12.0 ppm | 40 |
| YFM | 0.015 ppm | 100 |

Isopropyl N-[[methyl[[[2,3-dihydro-2,2-dimethyl-7-benzofuranyl]oxy]carbonyl]amino]thio]benzimidate

| Insect | Rate | % Mortality |
| --- | --- | --- |
| SAW | 31.3 ppm | 100 |
| CLO | 31.3 ppm | 100 |
| MBB | 31.3 ppm | 100 |

Ethyl N-[[methyl[[[[1-(methylthio)ethylidene]amino]-oxy]-carbonyl]amino]thio]-2,6-dichlorobenzimidate

| Insect | Rate | % Mortality |
| --- | --- | --- |
| SAW | 7.8 ppm | 100 |
| MBB | 3.9 ppm | 100 |
| TSSM | 250 ppm | 53 |
| CLO | 7.8 ppm | 83 |
| HF | 12.5 ppm | 73 |
| YFM | 0.5 ppm | 50 |

Ethyl N-[[methyl[[[[1-(methylthio)ethylidene]-amino]oxy]-carbonyl]amino]thio]benzimidate

| Insect | Rate | % Mortality |
| --- | --- | --- |
| SAW | 31.3 ppm | 100 |
| MBB | 31.3 ppm | 100 |
| CLO | 31.3 ppm | 100 |
| HF | 50.0 ppm | 100 |

Methyl N-[[methyl[[[2,3-dihydro-2,2-dimethyl-7-benzofuranyl-]oxy]carbonyl]amino]thio]benzimidate

| Insect | Rate | % Mortality |
| --- | --- | --- |
| SAW | 31.3 ppm | 100 |
| MBB | 31.3 ppm | 100 |
| CLO | 31.3 ppm | 100 |
| HF | 50.0 ppm | 100 |
| YFM | 0.50 ppm | 100 | n-Butyl N-[[methyl[[[2,3-dihydro-2,2-dimethyl-7-benzofuranyl-]oxy]carbonyl]amino]thio]benzimidate

| Insect | Rate | % Mortality |
| --- | --- | --- |
| SAW | 31.3 ppm | 100 |
| MBB | 31.3 ppm | 100 |
| CLO | 31.3 ppm | 100 |
| YFM | 0.50 ppm | 100 |
| HF | 50.0 ppm | 40 | n-Butyl N-[[methyl[[[2,3-dihydro-2,2-dimethyl-7-benzofuranyl-]oxy]carbonyl]amino]thio]-2-methylpropionimidate

| Insect | Rate | % Mortality |
| --- | --- | --- |
| SAW | 31.3 ppm | 100 |
| MBB | 31.3 ppm | 100 |
| CLO | 31.3 ppm | 100 |
| YFM | 0.50 ppm | 100 |
| HF | 50.0 ppm | 100 |

Phenyl N-[[methyl[[[2,3-dihydro-2,2-dimethyl-7-benzofuranyl-]oxy]carbonyl]amino]thio]benzothioimidate

| Insect | Rate | % Mortality |
| --- | --- | --- |
| SAW | 31.3 ppm | 100 |
| MBB | 31.3 ppm | 100 |
| CLO | 31.3 ppm | 50 |
| YFM | 0.03 ppm | 100 |
| HF | 50.0 ppm | 100 |

Phenyl N-[[methyl[[[[1-(methylthio)ethylidene]-amino]oxy]-carbonyl]amino]thio]benzothioimidate

| Insect | Rate | % Mortality |
| --- | --- | --- |
| SAW | 31.3 ppm | 73 |
| CLO | 15.6 ppm | 100 |
| YFM | 0.25 ppm | 93 |

Phenyl N-[[methyl[[[[1-(methylthio)ethylidene]amino]oxy]carbonyl]amino]thio]-2-methylpropiothioimidate

| Insect | Rate | % Mortality |
| --- | --- | --- |
| SAW | 31.3 ppm | 100 |
| MBB | 31.3 ppm | 100 |
| CLO | 31.3 ppm | 100 |
| HF | 50.0 ppm | 100 |
| YFM | 0.50 ppm | 80 |

The details of the mortality tests are as follows:

Preparation of tested chemicals—Analytical samples of each were dissolved in acetone. These acetone solutions were applied as such or portions of them were diluted with a Tween 20 "wet water" or a 10% sucrose "wet water". The "wet water" itself contained 0.132% v/v of Tween 20 (polyoxyethylene sorbitan monolaurate).

The southern armyworm and mexican bean beetle tests were effected with Henderson bush lima bean foliage characterized by two primary leaves per replicate. The leaves were dipped into a "wet water" emulsion of a test chemical, allowed to dry, and then placed on a moistened filter disk in a 9 cm plastic petric dish. Five larvae of the respective test insects were put on the leaves, the cover of the petri dish was replaced, and it was set aside for future evaluation. Three replications for each treatment rate were prepared.

The house fly test was effected by saturating a golf-ball size wad of cotton with 10 ml of a "10% wet sugar water" preparation of the test chemical. The saturated wad was placed in a portion cup which was attached to the inside surface of a 5-ounce waxed paper cup. Ten adult house flies were released in the 5-ounce cup and it was covered with a plastic lid for future observation. Two replicates were prepared for each treatment rate.

The yellow fever mosquito larvae test was effected by adding the appropriate amount of a wet water and acetone solution of the test chemical to 100 ml distilled water in a 5-ounce waxed paper cup. Ten mosquito larvae were added. Dried yeast was added after twenty-four hours. There were two replicates for each treatment rate.

The southern armyworm, mexican bean beetle, house fly and cabbage looper ova tests were held at 22° C., while the yellow fever mosquito larvae tests were held at 27° C.

The tests were evaluated for insect kill (including moribund and knocked down) after 24, 48 and sometimes 72 hours.

The foregoing test results indicate that the objectives of the invention have been satisfied and that a worthwhile contribution has been made to the pesticide art. They further indicate that the N-imidoylthio(methyl)-carbamates of formula I of this invention can be utilized for control of insect pests in the form of the pure compounds as prepared in the Examples, as technical grade compounds from commercial production, or as mixtures of the specific compounds. On the other hand, practical considerations indicate the desirability of providing those skilled in the pesticide art with formulations comprising a diluent carrier with or without adjuvants that will promote this distribution of the active compounds where pest control is desired and thus enhance efficacy and economics.

There are many different kinds of diluent carriers suitable for the method and formulation embodiments of this invention. Dispersible carriers are commonly used in the art. Such carriers may or may not include adjuvants such as wetting agents, emulsifying agents, stickers, and other components that indirectly promote efficacy.

The new carbamates of formula I are useful against insects, nematodes, and mites in formulations, e.g., as dusts, wettable powders, emulsifiable concentrates, aqueous dispersions, solutions, and flowable creams for application to a situs, soil, plants and foliage, seeds, or other parts of plants. Granular formulations can be prepared and applied to soil or on surfaces. Moreover, the new compounds of formula I of this invention can be the sole active agent in a formulation or other insecticidal, miticidal, or nematicidal components may be included.

The new solid compounds of formula I can be readily formulated as dusts by grinding a mixture of the compound and a pulverulent carrier in the presence of each other.

Representative suitable pulverulent carriers include the natural clays such as China, Georgia, Barden, Attapulgus, Kaolin, and Bentonite clays; minerals in their natural forms such as talc, pyrophillite, quartz, diatomaceous earth, Fuller's earth, chalk, sulfur, silica and silicates; chemically modified minerals such as washed bentonite and colloidal silica; and organic flours such as wood, walnut shell, soybean, cottonseed, and tobacco flours, and free flowing, hydrophobic starches. The proportions of pulverulent carrier and active compound of formula I can vary over a wide range depending upon the use of it, pests to be controlled and the conditions of treatment.

In general, dust formulations can contain up to about 90% (on a weight basis) of the active ingredient.

The dispersible powder formulations of this invention are prepared by incorporating a surfactant in a dust formulation prepared as described above. When about 0.1% to about 12% of a surfactant is incorporated in a dust, the dispersible powder thus obtained is particularly adapted for further admixture with water for spraying on inanimate matter and products, fruit trees, field crops, soil, and livestock. The dispersible powders can be admixed with water to obtain any desired concentration of active ingredient, and the mixture can be applied in amounts sufficient to obtain predetermined rates of application and uniform distribution. With this flexibility in mind, the dispersible powders of the invention can conveniently comprise preferably about 5% to about 80% of active ingredient.

Emulsifiable concentrates of the invention can be prepared by dissolving the active ingredient and a surfactant in a substantially water-immiscible solvent carrier, for example, cyclohexanone, methyl propyl ketone, aromatic hydrocarbons such as toluene, and xylene, and high-boiling petroleum hydrocarbons such as kerosene, diesel oil, and the like. If desired, a cosolvent such as methyl ethyl ketone, acetone, isopropanol, and the like can be included with a solvent carrier in order to enhance the solubility of the active ingredient. Aqueous emulsions are then prepared by mixing with water to give any desired concentration of active ingredient. The surfactants which can be employed in the aqueous emulsions of the invention are those types noted above. Mixtures of surfactants can be employed, if desired.

Advantageously, the concentration of active ingredient in the emulsifiable concentrates can range from about 5% to about 50% by weight, preferably from about 10% to about 40%.

The formulations containing new N-imidoylthio(methyl)carbamates of formula I according to the invention, can be applied to insects, mites, nematodes, soil or other situs by conventional methods. It will, of course, be appreciated that the conditions encountered when applying the method and formulations of this invention to actual practice can vary widely. Included among the variables that may be encountered are the degree of infestation by pests, the particular pest to be controlled, the particular situs being treated, the type of plants, the prevailing weather conditions, such as temperature, relative humidity, rainfall, dews, and so forth.

FORMULA

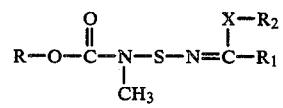
I

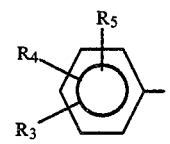
Ia

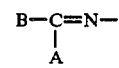
Ib

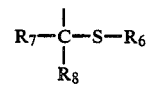
Ic

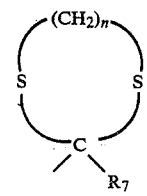
Id

-continued
FORMULA

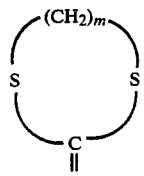   Ie

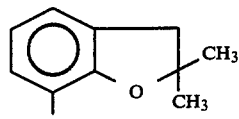

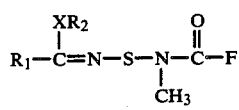 II

ROH   III

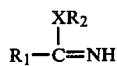 IV

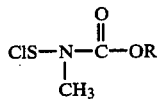 V

We claim:
1. A compound having the formula

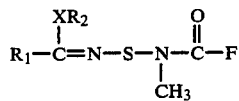 II wherein $R_1$ and $R_2$ are the same or different and are selected from the group consisting of alkyl of from one to ten carbon atoms, inclusive, phenyl, substituted phenyl comprising lower-alkyl-, lower-alkoxy-, halogen-, nitro-, or cyano-substituted phenyl, phenyl substituted lower-alkyl, and cycloalkyl; and X is oxygen or sulfur.

2. A compound according to claim 1 wherein $R_1$ and $R_2$ are the same or different and consist of alkyl of from one to four carbon atoms, inclusive, phenyl or substituted phenyl comprising lower-alkyl-, lower-alkoxy-, halogen-, nitro-, or cyano-substituted phenyl.

3. A compound according to claim 2 wherein $R_1$ is isopropyl; $R_2$ is phenyl, and X is sulfur so that the specific embodiment is phenyl N-[[methyl[fluorocarbonyl]amino]thio]-2-methylpropiothioimidate.

4. A compound according to claim 2 wherein $R_1$ is dichlorophenyl; $R_2$ is ethyl, and X is oxygen so that the specific embodiment is ethyl N-[[methyl[fluorocarbonyl]amino]thio]-2,6-dichlorobenzimidate.

5. A compound according to claim 2 wherein $R_1$ is phenyl; $R_2$ is ethyl, and X is oxygen so that the specific embodiment is ethyl N-[[methyl[fluorocarbonyl]amino]thio]benzimidate.

6. A compound according to claim 2 wherein $R_1$ is phenyl; $R_2$ is methyl, and X is oxygen so the specific embodiment is methyl N-[[methyl[fluorocarbonyl]amino]thio]benzimidate.

7. A compound according to claim 2 wherein $R_1$ is phenyl; $R_2$ is n-butyl, and X is oxygen so the specific embodiment is n-butyl N-[[methyl[fluorocarbonyl]amino]thio]benzimidate.

8. A compound according to claim 2 wherein $R_1$ is methylethyl; $R_2$ is n-butyl, and X is oxygen so the specific embodiment is n-butyl N-[[methyl[fluorocarbonyl]amino]thio]-2-methylpropionimidate.

9. A compound according to claim 2 wherein $R_1$ is phenyl; $R_2$ is phenyl, and X is sulfur so the specific embodiment is phenyl N-[[methyl[fluorocarbonyl]amino]thio]benzothioimidate.

10. A process for preparing a compound having the formula

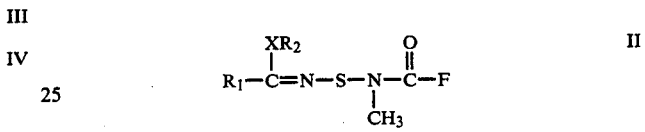 II wherein $R_1$ and $R_2$ are the same or different and are selected from the group consisting of alkyl of from 1 to 10 carbon atoms, inclusive, phenyl, substituted phenyl comprising lower-alkyl-, lower-alkoxy-, halogen-, nitro-, or cyano-substituted phenyl, phenyl substituted lower-alkyl and cycloalkyl; X is oxygen or sulfur which comprises contacting a compound having the formula

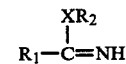

with N-chlorothio(methyl)carbamoyl fluoride.

11. A process according to claim 10 for preparing
phenyl N-[[methyl[fluorocarbonyl]amino]thio]-2-methylpropiothioimidate,
ethyl N-[[methyl[fluorocarbonyl]amino]thio]-2,6-dichlorobenzimidate,
ethyl N-[[methyl[fluorocarbonyl]amino]thio]benzimidate,
methyl N-[[methyl[fluorocarbonyl]amino]thio]benzimidate,
n-butyl N-[[methyl[fluorocarbonyl]amino]thio]benzimidate,
n-butyl N-[[methyl[fluorocarbonyl]amino]thio]-2-methylpropiothioimidate,
phenyl N-[[methyl[fluorocarbonyl]amino]thio]benzothioimidate,
methyl N-[[methyl[fluorocarbonyl]amino]thio]benzothioimidate,
n-butyl N-[[methyl[fluorocarbonyl]amino]thio]-2-methylpropionimidate.

* * * * *